(12) United States Patent
Kussow

(10) Patent No.: US 9,186,272 B1
(45) Date of Patent: Nov. 17, 2015

(54) CERVICAL COLLAR AND METHODS OF MANUFACTURE AND USE

(71) Applicant: Timothy Andrew Kussow, Mansfield, CT (US)

(72) Inventor: Timothy Andrew Kussow, Mansfield, CT (US)

( * ) Notice: Subject to any disclaimer, the term of this patent is extended or adjusted under 35 U.S.C. 154(b) by 342 days.

(21) Appl. No.: 13/651,457

(22) Filed: Oct. 14, 2012

(51) Int. Cl.
  *A61F 5/055*  (2006.01)
  *A61F 5/058*  (2006.01)

(52) U.S. Cl.
  CPC .............. *A61F 5/055* (2013.01); *A61F 5/05808* (2013.01); *A61F 5/05883* (2013.01)

(58) Field of Classification Search
  CPC ....................................................... A61F 5/055
  USPC ................ 128/869, 870, 876; 602/17, 18, 19; 2/468; 5/630, 636, 637, 640, 643, 622; 606/240; D29/100, 101.1, 101.2
  See application file for complete search history.

(56) References Cited

U.S. PATENT DOCUMENTS

| | | | | |
|---|---|---|---|---|
| 1,473,506 | A | * | 11/1923 | Nessler .......................... 607/109 |
| 2,865,434 | A | * | 12/1958 | Grenz ............................ 297/403 |
| 2,980,110 | A | * | 4/1961 | Brumfield et al. ................ 602/5 |
| 3,756,226 | A | * | 9/1973 | Calabrese et al. .............. 602/18 |
| 4,190,290 | A | * | 2/1980 | Strien ............................ 297/408 |
| 4,335,875 | A | * | 6/1982 | Elkin ............................... 482/74 |
| 4,401,111 | A | * | 8/1983 | Blackstone ..................... 602/18 |
| 4,691,917 | A | * | 9/1987 | Battista ......................... 482/131 |
| 4,789,154 | A | * | 12/1988 | Mattox ........................... 482/10 |
| 4,958,631 | A | | 9/1990 | Sarkozi |
| 4,966,136 | A | * | 10/1990 | Bates ............................. 602/18 |
| 5,005,563 | A | * | 4/1991 | Veale ............................. 602/18 |
| 5,005,564 | A | | 4/1991 | Grundei et al. |
| 5,211,623 | A | | 5/1993 | Sarkozi |
| 5,622,529 | A | | 4/1997 | Calabrese |
| 5,688,229 | A | | 11/1997 | Bauer |
| 5,795,315 | A | | 8/1998 | Traut et al. |
| 5,904,662 | A | | 5/1999 | Myoga |
| 6,058,517 | A | | 5/2000 | Hartunian |
| 6,423,020 | B1 | | 7/2002 | Koledin et al. |
| 6,923,778 | B1 | * | 8/2005 | Cheng ............................... 602/4 |
| 7,472,709 | B1 | * | 1/2009 | Nickerson ..................... 132/73.5 |
| 7,867,181 | B2 | | 1/2011 | Powell et al. |
| D633,624 | S | | 3/2011 | Monopoli |
| 7,901,327 | B2 | * | 3/2011 | Hargis et al. ..................... 482/10 |
| 8,672,818 | B2 | * | 3/2014 | Welch ........................... 482/132 |
| 8,708,416 | B2 | * | 4/2014 | Stronconi ...................... 297/397 |
| 8,845,565 | B1 | * | 9/2014 | Burns ............................... 602/4 |
| 2008/0004556 | A1 | | 1/2008 | Gehlbach et al. |
| 2012/0143110 | A1 | | 6/2012 | Maher et al. |

FOREIGN PATENT DOCUMENTS

EP  0 655 232 A1 * 10/1994

* cited by examiner

*Primary Examiner* — Alireza Nia
*Assistant Examiner* — Camtu Nguyen
(74) *Attorney, Agent, or Firm* — Dilworth IP LLC

(57) ABSTRACT

A cervical collar includes a flexible, elongate support member having two ends, a longitudinal axis, an initial length, and a plurality of slits near at least one end. Each slit defines a terminal segment of the support member and a connective link between the terminal segment and the remainder of the support member. A connector is provided for securing together the two ends. The support member may be manufactured by forming slits near at least one end of a flexible support member. The collar may be applied to a patient by providing a support member which is longer than is needed for the patient's neck, removing a terminal segment of the support member to adjust the length so that the support member is sized to appropriately encircle the patient's neck, flexing the support member around the patient's neck, and connecting the ends of the support member together.

2 Claims, 6 Drawing Sheets

CERVICAL COLLAR AND METHODS OF MANUFACTURE AND USE

FIELD OF THE INVENTION

The present disclosure relates generally to a collar useful for the support of a person's head and neck, a method of making the collar and a method of its use.

BACKGROUND

Serious neck injuries can have devastating impact on a patient and once a victim is injured and requires help, it is important for first responders to avoid compounding the initial injury through uncontrolled movement of the head and neck. For this purpose, a responder often applies a cervical collar to a neck injury victim. Since neck injuries are not always visually apparent, a cervical collar may be applied to a victim who is unconscious but who is suspected of having a neck injury or who was injured under circumstances in which such an injury is possible, such as an automobile accident or a fall.

A variety of cervical collars are known in the art. For example, U.S. Pat. No. 5,005,564 to Grundei et al., dated Apr. 9, 1991, discloses a cervical collar made of a foam material and with overlapping ends that join together my means of a hook-and-loop fastener. The collar is perforated at openings 3 to receive one or more support members 5. Without at least one support member, the collar offers only slight support and is used near the end of a patient's treatment, primarily to provide heating; to provide strong support, one or more support elements must be inserted in the openings (col. 1, lines 48-58).

U.S. Pat. No. 6,058,527 to Hartunian, dated May 9, 2000, discloses a sports neck brace made of a length of foam material in a split ring configuration having two ends which defined a vertical opening 20 which appears to permit placement around a player's neck, and having hook and pile fasteners 21, 25 and 27 to secure the two ends together in use (see, e.g., col. 3, line 57-col. 4, line 7). Thus this brace is not adapted to accommodate different sizes of necks.

SUMMARY OF THE INVENTION

The present invention resides in one aspect in a cervical collar which may include a flexible support member having an elongate configuration with two ends, a longitudinal axis and an initial length. The support member has a plurality of slits near at least one end, and each slit serves to define a terminal segment of the support member and a connective link between the terminal segment and the remainder of the support member. There is also a connecting means (e.g., a connector) for securing together the two ends of the support member.

Optionally, each end of the support member has an internal bore and the connecting means comprises a connecter sized for insertion into the internal bore to establish a friction fit therein.

In another aspect, the support member may comprise a polymeric foam material, e.g., a closed cell polymeric foam material.

In one embodiment, a connective link is dimensioned and configured to experience failure at an applied axial tension of not more than about 13 lbs.

According to another aspect, the invention provides a method for making a support member for a cervical collar. The method is practiced by forming a plurality of slits near at least one end of a flexible support member, optionally, at both ends. In one embodiment, the method may include forming a narrow middle region between the ends of the support member.

According to still another aspect, this invention provides a method for applying a cervical collar to a patient. This method is practiced by providing a support member having an initial length longer than is needed for the patient's neck, removing a terminal segment of the support member to adjust the length so that the support member is sized to appropriately encircle the patient's neck to inhibit movement of the patient's head when the ends of the support member are joined in abutting relation to each other; flexing the support member around the patient's neck; and applying a connector to join the ends of the support member together. Optionally but preferably, the ends of the support member are joined together in abutting relation to each other.

DETAILED DESCRIPTION

The present invention provides, in one aspect, a cervical collar which finds utility in stabilizing and/or immobilizing a victim's head and neck after a suspected neck injury. Cervical collars according to various embodiments of this invention provide significant advantages over cervical collars previously available for use in emergency neck injury response settings where immobilization is sought, and in therapeutic settings. By selecting materials for making a cervical collar as described herein, the cervical collar can be manufactured easily and inexpensively, is easily stored, is substantially resistant to the elements and so has a long effective life. Each cervical collar can be made to accommodate the largest of patients and so will find use with bariatric patients, but it can quickly and easily be adjusted in length to accommodate smaller persons as well, and so may be used with either bariatric or pediatric patients. The cervical collar can be applied to a patient found in a variety of positions without hyperextension or flexion of the patient's head or neck, which is a significant value in avoiding the exacerbation of neck injuries. In addition, the cervical collar allows for rapid extrication and so is suitable for movement of patients requiring assisted ventilation ("bag and drag" patients). The unassuming design and ease of use of the embodiments disclosed herein make such embodiments appear non-threatening to the patient and thus reduce patient stress as well as the stress of observers such as family members. In certain embodiments, the cervical collar may be made from water-buoyant material (a commercially available "pool noodle" or "woggle" was found to provide a basis for a functioning prototype) and so can also serve as a floatation device. Due to the low cost, a cervical collar as described herein can be treated as disposable and thus the costs and risks associated with re-use and disinfection are avoided. Other aspects of the invention relate to methods of making and applying a cervical collar.

Figure 1:
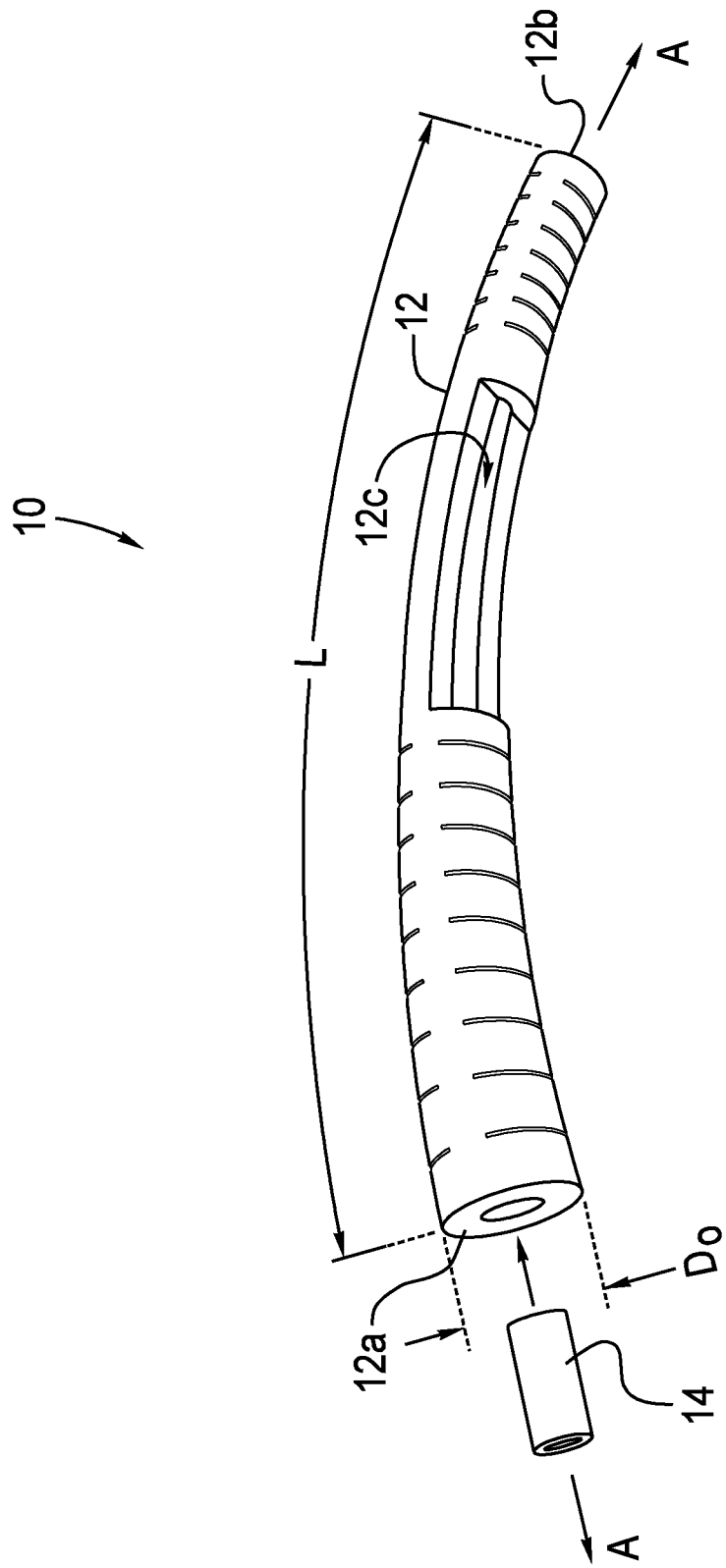
FIG. 1 is a perspective view of a cervical collar according to one embodiment of the invention.

One embodiment of a cervical collar according to the present invention is indicated generally at 10 in FIG. 1. The cervical collar 10 includes a support member 12 which is made from a flexible material and has an elongate configuration with a longitudinal axis A and an initial length L. The support member 12 has two ends: end 12a and end 12b. In the illustrated embodiment, the support member 12 has a generally tubular configuration with an outside diameter Do and an inside diameter Di. In one embodiment, the support member 12 is made from a foam material having a modulus of from about 35 psi to about 42 psi (measured per ASTM D3575-93) and a compression strength of from about 0.5 psi to about 19.0 psi (measured per ASTM D3575-93). For example, the support member 12 may be formed from the type of foam commonly used for pool noodles, e.g., closed-cell polyethylene foam. However, the invention is not limited in this regard and in other embodiments, other elastomeric, polymeric, or copolymeric foam materials, or other suitable materials, may be used, such as polyurethane foam, ethylene vinyl acetate (EVA) foam, etc.

The support member 12 is shown in FIG. 1 in a substantially linear configuration, prior to being manipulated into an annular configuration around a patient's neck.

The cervical collar 10 includes a connector 14 to provide a connecting means for securing together end 12a and end 12b, as will be described below. Suitable connectors are known in the art as hose connectors or tubing connectors and may be made of various materials, e.g., polyvinylchloride (PVC), nylon, or the like.

Figure 2:
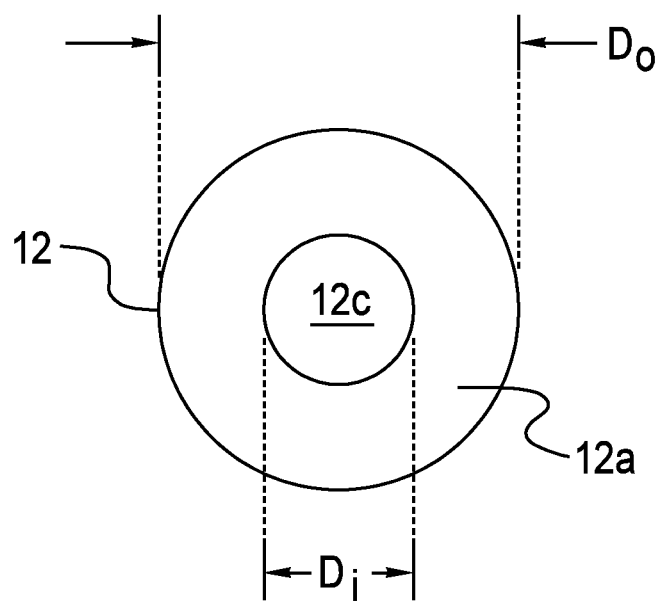
FIG. 2 is an end view of the support member of the cervical collar of FIG. 1.

The end view of FIG. 2 shows an internal bore 12c in end 12a, into which the connector 14 will be partially inserted. In the illustrated embodiment, the internal bore 12c is round and has a diameter Di, and the internal bore 12c extends for the entire length of the support member 12. The connector 14 is dimensioned and configured for a friction fit in internal bore 12c. Accordingly, the part of connector 14 protruding from end 12a after partial insertion into the internal bore 12c at one end of the support member 12 can be inserted into the internal bore 12c at the other end of the support member to secure the support member in an annular configuration around a patient's neck, as will be described below. The connector 14 may have any configuration effective to provide the friction fit. For example, when internal bore 12c is round, the connector 14 may be a cylindrical plug; optionally, the connector 14 may be formed to have ribs or barbs or a serrated or other textured surface or feature to resist removal from the internal bore 12c, as is common in commercially available connectors. In yet another embodiment, end 12a and end 12b each has a separate bore to receive the connector 14, rather than a single bore extending the entire length L.

Figure 3A:
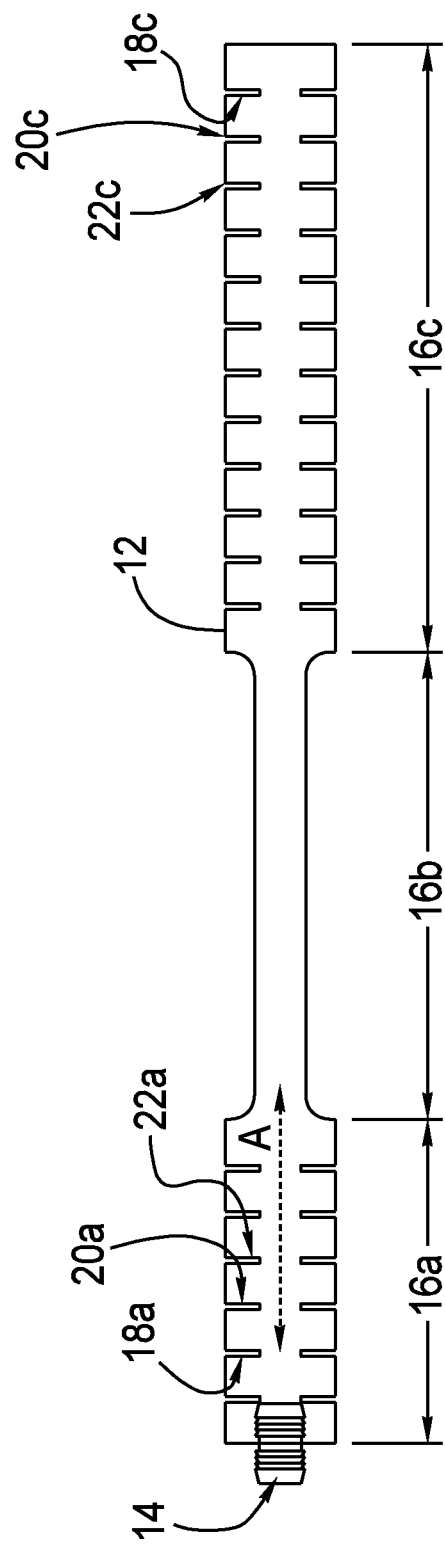
FIG. 3A is a top view of the support member of the cervical collar of FIG. 1.

Referring now to FIG. 3A, the support member 12 is seen to have three principal regions: two end regions and a middle region, i.e., end region 16a, middle region 16b and end region 16c. The end region 16a has a plurality of slits 18a, 20a, 22a, etc., and the end region 16c has a plurality of slits 18c, 20c, 22c, etc. Each slit is disposed generally transversely to the longitudinal axis A.

Figure 3B:
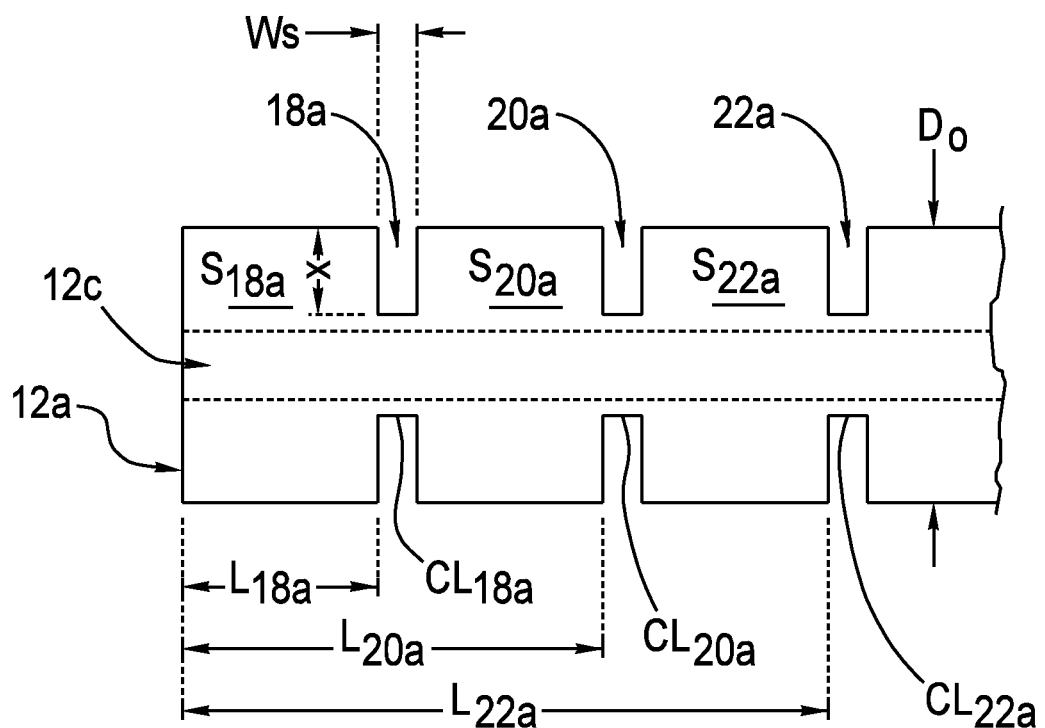
FIG. 3B is a detail view of a portion of FIG. 3A.

As shown in the detailed view of FIG. 3B, each slit 18a, 20a, etc., has a width Ws and serves to define a terminal segment S18a, S20a, S22a, etc. of the support member 12 between the slit and the end 12a or the adjacent terminal segment. Each slit 18a, 20a, etc., also serves to define a connective link CL18a, CL20a, CL22a, etc., between the adjacent terminal segment S18a, etc., and the remainder of the support member 12. The depth x of each slit 18a, etc. is selected in relation to the material from which the support member 12 is dimensioned and configured to substantially reduce the tensile strength of the support member at the corresponding connective link CL18a, etc. to facilitate removal of the distal adjacent terminal segment S18a, etc., by breaking the connective link, e.g., by pulling the terminal segment away from the adjacent terminal segment or from the middle region 16b, possibly by hand. For a specific example, slit 18a is dimensioned and configured so that a user (e.g., a first responder) can grasp terminal segment S18a in one hand and terminal segment S20a in the other hand and then tear terminal segment S18a from the remainder of the support member 12 using a manual twisting and/or pulling action. For example, in one embodiment, one or more slits 18a, etc., are dimensioned and configured to provide connective links CL18a, etc. that are dimensioned and configured so that the connective links will experience failure at an applied axial tension of not more than about 6 kilograms (kg) (about 13 pounds (lb), optionally not more than about 5 kg (about 11 lb). In one embodiment, a connective links will experience failure at an applied axial tension of about 5 kg to about 6 kg to facilitate removal of a terminal segment S18a, etc. by hand. However, the invention is not limited in this regard and in other embodiments, a tool may be used. Removal of a terminal segment S18a, etc. serves to reduce length L by a corresponding terminal length L18a, L20a, L22a, etc. The newly exposed end then functions as the original end 12a or 12b but the support member 12 then has an adjusted (i.e., reduced) length L.

While the illustrated embodiment has a plurality of slits 18a, etc. at both ends 12a and 12b of the support member 12, the invention is not limited in this regard and in other embodiments, there may be a plurality of slits only at one end. When there are slits 18a, etc. at an end 12a or 12b of the support member 12, the internal bore 12c at that end is coextensive with the slits so that upon removal of a terminal segment S18a etc. the exposed internal bore can securely receive the connector 14.

Figure 4:
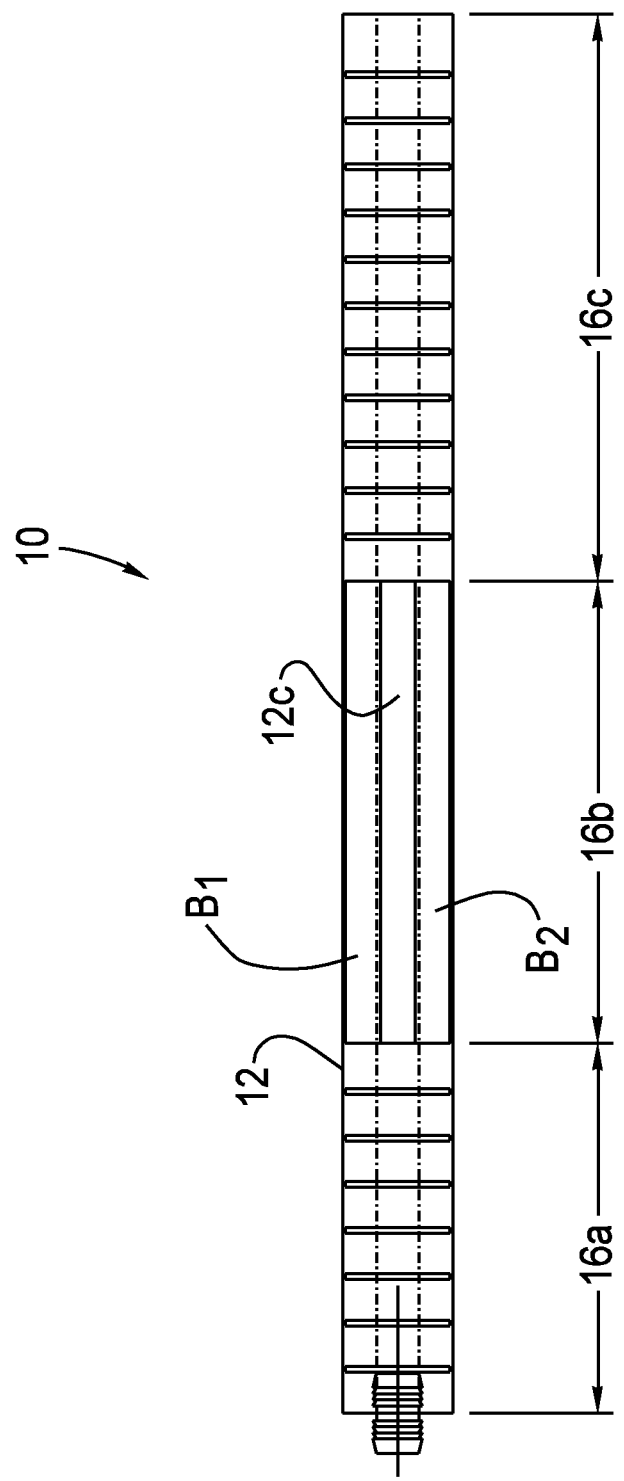
FIG. 4 is a side elevation view of the support member of the cervical collar of FIG. 1.

Referring again to FIG. 3A, the middle region 16b of the support member 12 has an optionally narrowed configuration relative to the end region 16a and the end region 16c. In FIG. 4 it can be seen that in one embodiment, the width of middle region 16b is less than Di and so is small enough to expose the internal bore 12c. The middle region 16b therefore consists of a first bridge portion B1 and a second bridge portion B2 which together join end region 16a to end region 16c. So configured, the middle region 16b provides a region of enhanced flexibility and allows air circulation to dissipate body heat from around the neck. The exposure of the internal bore also allows the responder to visualize the neck and so better monitor the patient's condition.

The relative lengths of end region 16a, middle region 16b and end region 16c are not critical and will vary in use as a user removes a terminal length from end 12a and/or end 12b. In one embodiment, the length of middle region 16b may be about one-third of the length L of support member 12. The lengths of end region 16a and end region 16c may be the same as, or different from, each other. In one embodiment, the length of end region 16a is about one-half the length of end region 16c prior to the removal of any terminal length from either end.

In one specific embodiment, various dimensions of support member 12 may be as approximately as follows: L=30 inches (in.) (76 centimeters (cm)); the length of end region 16a=7 in. (18 cm); the length of middle region 16b=10 in. (25 cm); the length of end region 16c=13 in. (33 cm); Do=2.375 in. (6 cm); Di=1 in. (2.5 cm); Ws=0.125 in. (0.3 cm); and the distance between slots (i.e., the width of segments between slots)=1 in. (2.5 cm). None of these dimensions is critical and they may be varied to suit manufacturing needs, patient needs, user needs, etc. Preferably, the support member 12 is configured so that it provides adequate protection to the wearer without the need for additional reinforcing structures, as required in U.S. Pat. No. 5,005,564 to Grundei et al. (supra).

One method of making a support member 12 is to use a length of hollow extruded polymer foam tubing of an overall length suitable for the largest anticipated patient, and cut a plurality of slits near at least one end to define an end region near that end, optionally near both ends. Optionally, the method may include identifying a middle region and narrowing the middle region. Cutting slits and narrowing the middle region may be done using cutting techniques suitable to the material from which the support member 12 is made. Methods for cutting and otherwise working polymer foams are known in the art and include, for example, sawing, die-cutting, hot-knifing, water jet cutting and welding.

Figure 5:
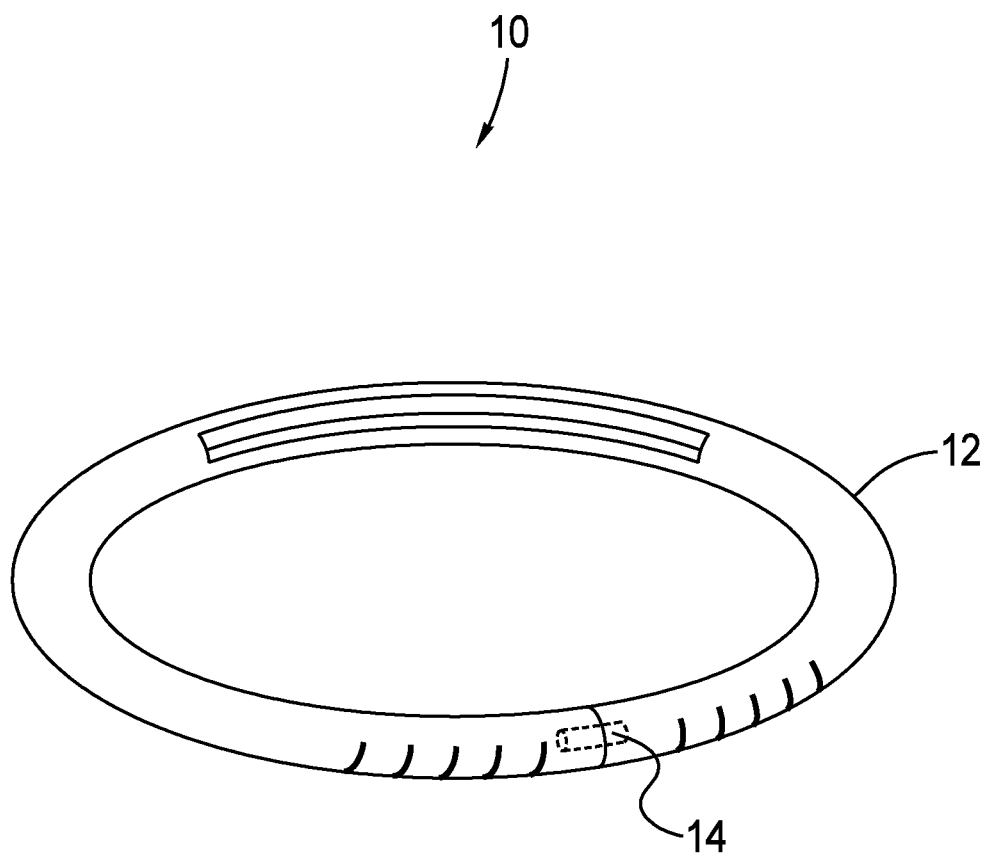
FIG. 5 is a schematic perspective view of the cervical collar of FIG. 1 in a closed loop configuration with the ends interconnected by the connecter, as it would be in use.

In use, to apply the cervical collar 10, the support member 12 may be placed against a victim's neck, preferably without moving the victim's head. The user sizes the support member 12 to the victim's neck by removing at last one terminal segment S18a etc. from the support member 12. When the internal bore 12c at an end 12a or 12b of the support member 12 is coextensive with slits 18a etc. at that end, a connector 14 may be securely received in the internal bore despite removal of a terminal segment from that end to adjust the length of the support member. The connector 14 is partially inserted into an internal bore 12c at one end 12a or 12b of the support member 12 and the support member is bent around the victim's neck so that the protruding part of the connector can be inserted into the other end of the support member. The resulting configuration for the cervical collar 10 is illustrated in FIG. 5, wherein it can be seen that the ends 12a, 12b of the support member 12 are in end-to-end abutting relation to each other, rather than in an overlapping configuration. Accordingly, the overall diameter of the cervical collar 10 is generally uniform (Do), i.e., the joint where end 12a meets end 12b does not create a region around the victim's neck where the cervical collar is larger in diameter than elsewhere. Preferably, the middle region 16b is centered against the back of the patient's neck. The assembled cervical collar 10 will inhibit movement of the victim's head relative to the shoulders and thus inhibit subsequent injury or the exacerbation of injury to the victim's neck.

The terms "first," "second," and the like, herein do not denote any order, quantity, or importance, but rather are used to distinguish one element from another. The terms "a" and "an" herein do not denote a limitation of quantity, but rather denote the presence of at least one of the referenced item.

Although the invention has been described with reference to particular embodiments thereof, it will be understood upon a reading and understanding of the foregoing disclosure by one of ordinary skill in the art that numerous variations and alterations to the disclosed embodiments will fall within the scope of this invention and of the appended claims.

What is claimed is:

1. A method for applying a cervical collar to a patient, comprising:
    providing a support member having two ends and an initial length longer than is needed for the patient's neck;
    removing a terminal segment of the support member to adjust the length so that the support member is sized to appropriately encircle the patient's neck to inhibit movement of the patient's head when the ends of the support member are joined in abutting relation to each other; flexing the support member around the patient's neck; and
    applying a connector to loin the ends of the support member together;
    wherein the support member has an elongate configuration with two ends, a longitudinal axis, an internal bore and an initial length, and a plurality of slits near at least one end, the slits being coextensive with the internal bore; and wherein each slit serves to define the terminal segment of the support member, a remainder of the support member and a connective link between the terminal segment and the remainder of the support member; and wherein removing the terminal segment comprises exposing an internal bore and applying the connector comprises inserting the connector into the internal bore.

2. A cervical collar comprising:
    a flexible support member having an elongate configuration with two ends, a longitudinal axis, an internal bore and an initial length, and having a plurality of slits near at least one end, the slits being coextensive with the internal bore;
    each slit serving to define a terminal segment of the support member, a remainder of the support member and a connective link between the terminal segment and the remainder of the support member; and
    connecting means for securing together the two ends of the support member;
    wherein each end of the support member has an internal bore and the connecting means comprises a connector sized for insertion into the internal bore to establish a friction fit therein.

* * * * *